United States Patent [19]

Biere

[11] Patent Number: 4,705,857

[45] Date of Patent: Nov. 10, 1987

[54] INDOLE DERIVATIVES, PROCESS FOR PRODUCING THEM AND THEIR USE AS INTERMEDIATES

[75] Inventor: Helmut Biere, Berlin, Fed. Rep. of Germany

[73] Assignee: Schering Aktiengesellschaft, Berlin and Bergkamen, Fed. Rep. of Germany

[21] Appl. No.: 547,555

[22] Filed: Oct. 28, 1983

[30] Foreign Application Priority Data

Oct. 29, 1982 [DE] Fed. Rep. of Germany ....... 3240513

[51] Int. Cl.$^4$ .................. C07D 491/04; C07D 498/00; C07D 209/56; C07D 209/36
[52] U.S. Cl. ...................................... 546/65; 548/414; 548/430; 548/131; 548/495; 548/496; 546/198; 546/201; 546/86; 546/87; 544/142; 544/143; 544/144; 544/372; 544/373
[58] Field of Search .................. 546/201, 86, 87, 113, 546/198, 65; 544/143, 144, 373, 372; 548/131, 427, 484, 483, 414, 430, 496, 495

[56] References Cited

PUBLICATIONS

J. of Org. Chemistry, vol. 44, pp. 3741–3744, 1979.
The Condensed Chemical Dictionary, 3rd Ed., Gessner G. Hawley, p. 86.
J. March, Advanced Organic Chemistry, 2nd Ed., 1977, pp. 805–806.

Primary Examiner—Henry R. Jiles
Assistant Examiner—J. Richter
Attorney, Agent, or Firm—Millen & White

[57] ABSTRACT

Indole derivatives of formula I

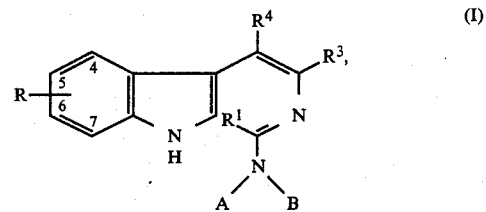

R is hydrogen, one or two halogen atoms or one or two organic radicals in the 4-, 5-, 6- or 7-position(s),
$R^1$ and $R^4$ are the same or different and each is hydrogen, alkyl of 1 to 3 carbon atoms or alkoxyalkyl of 1 to 3 carbon atoms in each of the alkoxy and alkyl portions,
$R^3$ is phenyl, —COOalkyl, —PO$_3$(alkyl)$_2$, —SO$_2$aryl, —SO$_2$alkyl,

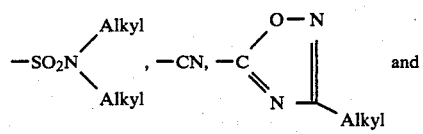 and

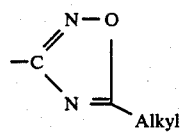

each of 1 to 3 carbon atoms in each alkyl group, and A and B each independently is alkyl of 1 to 3 carbon atoms or together with the connecting N-atom form a pyrrolidono, piperidino, morpholino or piperazino group, are valuable intermediates for preparing valuable tryptophans and β-carbolines.

18 Claims, No Drawings

INDOLE DERIVATIVES, PROCESS FOR PRODUCING THEM AND THEIR USE AS INTERMEDIATES

CROSS REFERENCE TO RELATED APPLICATION

This application is related to commonly assigned, U.S. application Ser. No. 546,356, filed on even date, whose entire disclosure is incorporated by reference herein.

BACKGROUND OF THE INVENTION

The present invention relates to new indole derivatives, a process for producing them and their use to prepare valuable compounds.

Carboline derivatives, especially substituted β-carboline derivatives, have recently aroused great interest in pharmacological research since they exert a wealth of therapeutically useful effects on the central nervous system. For example, they display anticonvulsive, anxiolytic, muscle relaxing and/or sedative effects.

The importance that is given to this class of substances is further reflected in the great number of patent applications filed, of which the following are examples: DE-OS No. 30 15 816, DE-OS No. 30 23 567, DE-OS No. 30 48 318 and U.S. Pat. No. 3,302,667.

The substituted tryptophans for example, have a sleep inducing effect. Tryptophan is widely used, for example, as an additive to infusion solutions, animal feed, etc.

The processes that are described in the literature for the production of β-carbolines and tryptophan derivatives have the drawback that they go through several stages and are not always satisfactory in yields (R. A. Abramovitch and J. D. Spenser, Advances in Heterocycl. Chemistry, Vol. 3, p 79).

A typical carboline and tryptophan synthesis can be summarized by the diagram on the next page.

Scheme of formulas

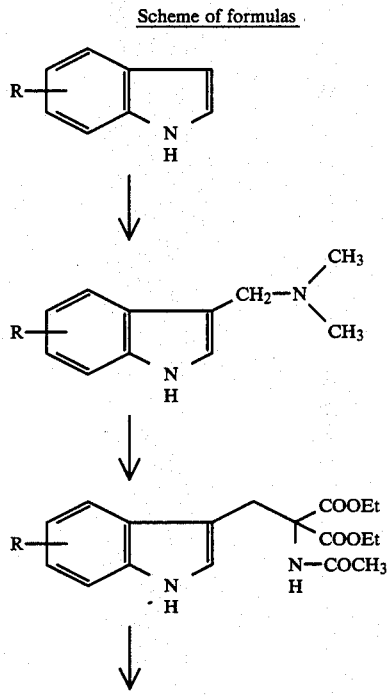

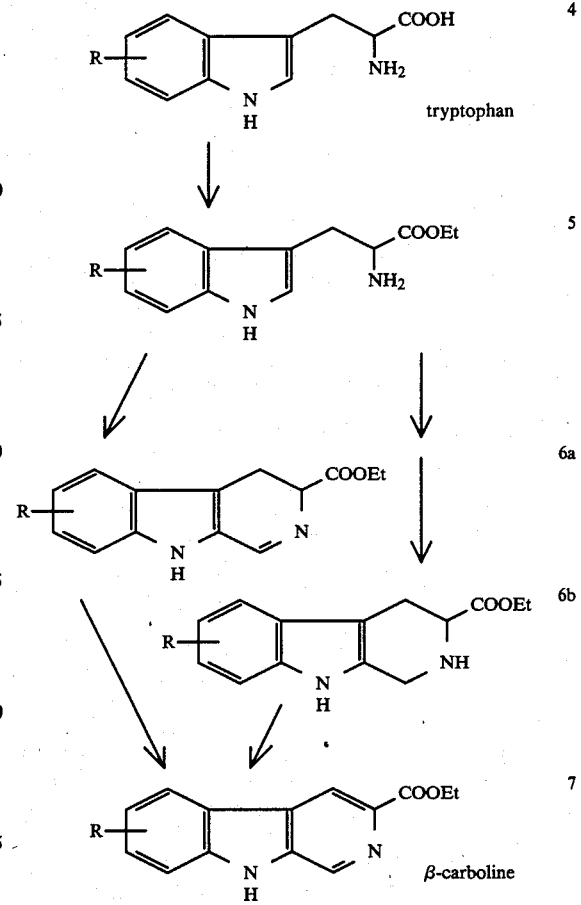

Starting with indole (1), gramine or a compound analogous to gramine (2) is produced by reaction with formaldehyde and a secondary amine. This is converted into a tryptophan precursor (3) by reaction with acetoamidomalonic ester under basic catalysis.

Racemic tryptophon (4) is formed after elimination of all protective groups and decarboxylation. Tryptophan ester (5) is formed after esterification, from which a 3,4-dihydro-β-carboline (6a) is formed after acylation of the amino group and cyclization under Bischler-Napieralski reaction conditions, and a tetrahydro-β-carboline (6b) is formed according to Pictet-Spengler. It is converted into the carbolines (7) after dehydration.

Apart from the large number of synthesis steps with the inevitable loss of time and yield, the cyclizations according to Bischler-Napieralski and Pictet-Spengler, cause special problems. Despite numerous improvements in these processes, only a slight yield results, whereby sensitive, partially hydrogenated intermediate products are formed which can cause various secondary reactions. Also, the dehydrogenation reaction to form di- and tetrahydrocarbolines often results in a low yield.

For this reason, it would be considered a particularly important advance in process engineering, if it were possible to perform a ring closure reaction on unsaturated indole precursors, exemplified by dehydrotryptophan derivatives, whereby a simple production process would be a prerequisite for the required dehydrotryptophan derivatives.

It would be a further important advance in process engineering, if it were possible to perform this ring closure reaction on a dehydrotryptophan derivative in such a way that the aromatic carboline system would be formed instead of a 1,2-dihydrocarboline derivative.

SUMMARY OF THE INVENTION

Accordingly, it is an object of this invention to provide unsaturated carboline precursors which make a smooth ring closure reaction for preparation of the aromatic carbolines possible.

Upon further study of the specification and appended claims, further objects and advantages of this invention will become apparent to those skilled in the art.

These objects have been achieved by providing indole derivatives of formula I:

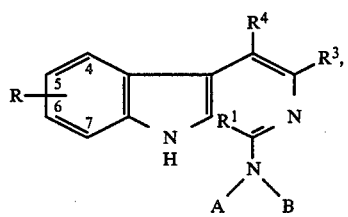

wherein

R is hydrogen, one or two of halogen atoms or any organic radicals in the 4-, 5-, 6- or 7- position(s), $R^1$ and $R^4$ are the same or different, and each is hydrogen, alkyl of 1 to 3 carbon atoms or alkoxyalkyl, with 1 to 3 carbon atoms in each of the alkoxy and alkyl portions, $R^3$ is phenyl, —COOalkyl, —PO$_3$(alkyl)$_2$, —SO$_2$aryl, —SO$_2$alkyl

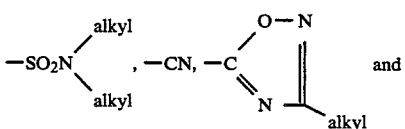

and

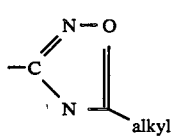

of 1 to 3 carbon atoms in each alkyl radical and A and B, each alone is alkyl of 1 to 3 carbon atoms, or together with the connecting N-atom form a pyrrolidino, piperidino, morpholino or piperazino group.

These objects have also been achieved by providing a process for producing (a) β-carbolines of Formula IV

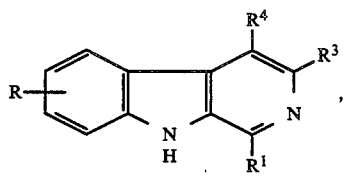

wherein R, $R^1$, $R^3$ and $R^4$ are as defined for formula I, and (b) tryptophan derivatives of Formula V

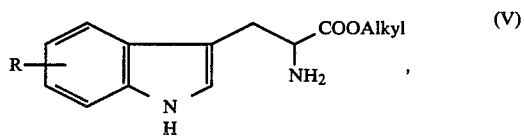

wherein R is as defined for formula I.

DETAILED DISCUSSION

It has now been found, on the one hand, that the new indole derivatives of formula I, as dehydrotryptophan derivatives, are important intermediates for production of tryptophan and tryptophan analogs, e.g., of formula V ($R^4$=H, $R^3$=COOalkyl). For example, by catalytic hydrogenation, or, optionally by asymmetrical hydrogenation on chiral rhodium catalysts which are known in the literature, they can be converted into optically active tryptophan precursors. The latter yield tryptophan or its analogs after hydrolysis of the ester and amidine groups. Catalytic hydrogenation preferably is accomplished on rhodium catalysts and preferably access on by means of weak acids. See, e.g., *J. Org. Chem.*, 44, 1979, 3741-3748; and *J. Org. Chem.*, 47, 1982, 94.

All of the tryptophan derivatives preparable by this invention are either useful themselves, e.g., as sedatives, or can be used conventionally to prepare other tryptophan derivatives of this invention which are so useful.

It has further been found, on the other hand, that the new indole derivatives of formula I are valuable precursors for cyclization to form the desired β-carbolines (e.g., 8-aza-βcarboline-3-carboxylic acid-ethyl ester) of formula IV, e.g., by elimination of

The cyclization results in a good yield both under thermal load per se and by heating under catalytic conditions.

Using a purely thermal load method, the indole derivative of formula I is heated to 150°-250° C., preferably 180°-220° C., under vacuum where appropriate. Alternatively, the indole derivative can be heated in a solvent having a high boiling point such as quinoline or diphenyl ether under reflux. Carboline formation is also observed if the indole derivative is loaded onto a support, for example, silica gel, using an easily volatile solvent, for example, dichloromethane, and the support containing the material is heated to around 180°-210° C. This can also suitably be performed with the coils of a bulb tube furnace. Typical reaction times are 15-120 minutes preferably.

Catalyzed reactions to form β-carbolines primarily include proton catalyzed conversions. These conversions are performed, e.g., by heating preferaby 0.1 to 10 mmole per ml of solution of the indole derivative to a preferred temperature of 100°-160° C., for example, in organic acids, for example, formic acid, acetic acid, propionic acid or trifluoroacetic acid, or in an inorganic medium, for example, phosphoric acid, polyphosphoric acid or phosphorus oxychloride, preferably for 1-20 hours. Inert organic solvents, for example, toluene, ethyl acetate, dioxane, dimethoxyethane, acetonitrile, among others, can be used as diluents.

The resulting substituted carboline derivatives can be further substituted by other known chemical processes or the existing substituents can be varied further, also conventionally. Hence, the process according to this invention makes easily available a large number of β-carboline derivatives.

The substituent R in formulae I, II, IV and V can be in 4-, 5-, 6- or 7- position(s), of the aromatic ring, whereby the ring can be mono- or disubstituted with the substituent R. R can be hydrogen, halogen or any organic radical.

Fluorine, chlorine, bromine and iodine are suitable halogen atoms. Suitable organic radicals preferably include: alkyl, alkoxyalkyl or alkoxy each of 1 to 4 carbon atoms, methylenedioxy, benzyloxy, aza, cyano, or alkoxycarbonyl or dialkylamino, each of 1 to 4 carbon atoms in each alkyl portion. Suitabe aryl groups include phenyl, α- or β-naphthyl, etc.

Many other substituents are possible and are all disclosed in many references, e.g., DE-OS No. 30 15 816, DE-OS No. 30 23 567, DE-OS No. 30 48 318, U.S. Pat. No. 3,202,667, U.S. Ser. No. 331,740, filed on Dec. 17, 1981, now allowed, and U.S. Pat. No. 4,371,536, all of whose entire disclosures are incorporated by reference herein. The references also disclose in detail the pharmacological utility of all the compounds preparable by the process of this invention for preparing β-carbolines.

The indole derivatives of formula I of this invention can be prepared in one step by reaction of an indole of formula II

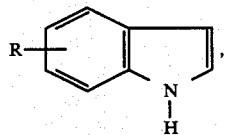
(II)

wherein R is as defined in formula I, with an azabutadiene of formula III

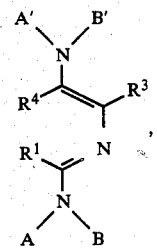
(III)

wherein a' and B' are the same or different from A and B and are selected from the groups defined for A and B and $R^1$, $R^3$, $R^4$ and A and B are as defined for formula I, in the presence of acids at an effective temperature of 0°–100° C.

Liquid organic acids and some inorganic acids are particularly suitable for use as solvents and catalysts simultaneously, i.e., the indole and azabutadiene can be heated in organic acids, for example, formic acid, acetic acid, propionic acid, trifluoroacetic acid, among others, or inorganic acids, e.g., phosphoric acid, polyphosphoric acid or phosphorus oxychloride, alone or in admixture with other inert solvents, for example, dichloromethane, tetrahydrofuran, dioxane, dimethoxyethane, ethyl acetate, acetonitrile, etc. It is also possible to use catalytic amounts preferably, 2–5 mmole per ml of solution, of inorganic acids such as sulfuric aci , hydrochloric acid, perchloric acid, etc., in inert solvents (as above). The optimal effective reaction temperature is somewhat variable depending on the catalysts or solvents chosen; however, it generally is 0° to 100° C, for example, in trifluoroacetic acid it is 0° to 50° C., preferably at room temperature. Preferred reaction times are 8–24 hours. Choice of the reaction conditions is also governed by the substituents present in the indole. Electron donor substituted indoles generally react faster and therefore under more gentle conditions than acceptor substituted indoles.

In general, by "effective temperature" is meant one which effects the reaction of the compounds of formulae II and III to form one of formula I. If temperatures higher than such effective temperatures are chosen, the resultant reaction (cyclization) and products (β-carbolines) will be those which are the subject of commonly assigned U.S application Ser. No. 546,356.

The amount of azabutadiene is preferably 1.2 to 2.0 equivalents per mole of indole. Preferably, the concentration of total reactants in the acid and/or inert solvent is 10–50 wt %. The reaction is preferably carried out under an inert atmosphere, e.g., nitrogen.

The acids generally are strong acids and the solution pH's are preferably 0–5.

The process of this invention is generally disclosed in terms of its broad application to the preparation of the compounds of Formula I. Occasionally, for certain substituents R, which will be readily recognized by those skilled in the art, conventional modifications may be necessary, e.g., appropriate protection of interfering groups. Typically the process is conducted analogously to the procedures of *Angew. Chem.*, 93, 1981, 297 etc.

All of the starting materials are either per so known or are conventionally preparable using fully conventional methods from other known or readily preparable starting materials, e.g., analogous to the methods used for azadienes 1–4 below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Production of the azabutadienes of formula III is demonstrated by the following examples:

(1)
3-dimethylamino-2-(dimethylaminomethyleneamino)-ethyl acrylate (azadiene 1)

(a) Preparation is according to W. Kantlehner et al., Liebigs Ann. Chem. 1980, 344 whose disclosure is incorporated by reference herein.

(b) 3.1 g of freshly distilled glycine ethyl ester is mixed with 17.7 g of dimethylformamidediethylacetal and 0.3 g of potassium tert-butylate and is heated first at 80° C. (bath temperature), then gradually to 160° C. (bath temperature), whereby the resulting alcohol and other readily volatile components are distilled off. After 5 hours, the residue is fractionated in a high vacuum, then distilled once more in a bulb tube. Yield: 3.6 g (54%); boiling point, 150°–160° C. (at 0.05 torr), gas chromatographic purity 97%; $n_D^{25}$ 1.5550.

(2)

3-dimethylamino-2-(dimethylaminomethyleneamino)-crotonic acid-ethyl ester) (azadiene 2)

A mixture of 4.7 g of N-(dimethylaminomethylene)-glycine-ethyl ester (W. Kantlehner et al., Liebigs Ann Chem. 1980, 344), 8 g of dimethylacetamide-dimethylacetal and 0.4 g of potassium tert-butylate, analogously to 1b), is heated for 8 hours with distilling off of the resulting alcohols. The residue is then fractionated.

(3)

2-dimethylamino-1-(dimethylaminomethyleneamino)-ethylene-phosphoric acid-diethyl ester (azadiene 3)

A mixture of 3.7 g of aminomethane phosphonic acid-diethyl ester and 15 g of the aminal ester tert-butoxy-N,N,N', N'-tetramethylmethanediamine is heated for 6 hours to around 160° C. After fractional distillation of the residue in a bulb tube at 160°–165° C. and 0.03 mm, 4.2 g (69%) of the compound of the title is obtained.

(4) N²-(2-dimethylamino-1-phenylvinyl)-N¹, N¹-dimethylformamidine (azadiene 4)

Preparation is according to W. Kantlehner et al., Liebigs Ann. Chem., 1980, 344.

The following examples will explain the process according to the invention in more detail.

EXAMPLE 1

2-(dimethylaminomethyleneamino)-3-(3-indolyl)-ethyl acrylate (a) 2.3 g of indole and 6.4 g of azadiene 1 are dissolved in 40 ml of trifluoroacetic acid, with ice cooling, and stirred for 48 hours at room temperature. The product is poured into ice water, neutralized with sodium bicarbonate solution and extracted with ethyl acetate. After concentration of the organic phase, the residue is chromatographed by a silica gel column with ethyl acetate and finally recrystallized from toluene. 2 g (35%) of the product with a melting point of 138° C. is obtained.

(b) 1.3 g of azadiene 1 is dissolved in 10 ml of dichloromethane and mixed with 4.5 ml of trifluoroacetic acid with ice cooling. After addition of 0.47 g of inhole, it is stirred for 2 hours at 0° C., then 72 hours at room temperature. After treatment as above, 650 mg (57%) of the product, with a melting point of 137° C. (toluene) is obtained.

EXAMPLE 2

2-(dimethylaminomethyleneamino)-3-(5-benzyloxy-3-indolyl)-ethyl acrylate 2.2 g of 5-benzyloxyindole and 3.6 g of azadiene 1 are moderately heated to 50° C. in 17 ml of glacial acetic acid for 24 hours. After treatment, 2.5 g (65%) of the product with a melting point of 140° C. (toluene) is obtained.

EXAMPLE 3

2-(dimethylaminomethyleneamino)-3-(4-cyano-3-indolyl)ethyl acrylate 320 g of azadiene 1 is mixed with 2.5 ml of trifluoroacetic acid and stirred for 10 minutes at room temperature. Then, 140 mg of 4-cyano-indole is added and the solution is heated for 1 hour under nitrogen to 80°. After treatment, 140 mg (45%) of the product with a melting point of 159° C. (ethanol) is obtained.

EXAMPLE 4

1-(dimethylaminomethyleneamino)-2-(3-indolyl)-ethylenephosphoric acid-diethyl ester Production results, analogously to example 1 (b), from indole and azadiene 3.

Use of the compounds of formula I for the preparation of β-carbolines of formula IV is explained by the following examples.

(1) β-carboline-3-carboxylic acid-ethyl ester (a) 285 mg of the indole derivative prepared by example 1 is heated in a bulb tube apparatus under a vacuum of about 100 torr for 1 hour at 200°–210° C. After cooling, the reaction product is dissolved in toluene/tetrahydrofuran and filtered with silica gel and finally recrystallized from acetonitrile. 120 mg (50%) of the title compound with a melting point of 233°–235° C. is obtained.

(b) The above mentioned β-carboline ester is also obtained when the indole derivative (example 1) is dissolved in quinoline and heated for 6 hours to 200° C.

(c) The above mentioned β-carboline ester is also obtained when the indole derivative (example 1) is dissolved in a little dichloromethane, picked up on silica gel and the material is heated in a bulb tube for 1 hour to 200° C.

(d) The above mentioned β-carboline ester is also obtained, when the indole derivative (example 1) is heated in trifluoroacetic acid to about 80° C.

(e) The above mentioned β-carboline ester is also obtained when the indole derivative (example 1) is heated in glacial acetic acid at reflux.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications fo the invention to adapt it to various usages and conditions.

What is claimed is:

1. An indole derivative of the formula wherein

R is hydrogen or one or two of halogen atoms, alkyl, alkoxyalkyl or alkoxy each of 1 to 4 carbon atoms, methylenedioxy, benzyloxy, aza, cyano, or alkoxycarbonyl or dialkylamino, each of 1 to 4 carbon atoms in each alkyl portion, in the 4-, 5-, 6- or 7-position(s), R[1] and R[4] are the same or different and each is hydrogen, alkyl of 1 to 3 carbon atoms or $C_{1-3}$-alkoxy-$C_{1-3}$-alkyl, R[3] is phenyl, —COOalkyl, —PO$_3$(alkyl)$_2$, —SO$_2$aryl, —SO$_2$alkyl,

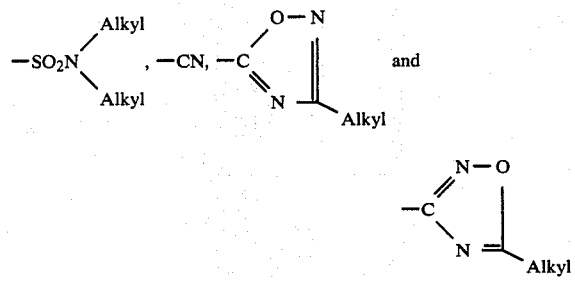

wherein each alkyl is of 1–3 C-atoms and aryl is phenyl or α- or β-naphthyl, and
A and B each independently is alkyl of 1 to 3 carbon atoms, or together with the connecting N-atom form pyrrolidino, piperidino, morpholino or piperazino.

2. A compound of claim 1 wherein R is H or benzyloxy.

3. A compound of claim 1 wherein R[4] is H.

4. A compound of claim 1 wherein R[3] is phenyl, —COOalkyl or —PO$_3$(alkyl)$_2$.

5. A compound of claim 1 wherein A and B each independently is alkyl of 1–3 C-atoms.

6. 2-(dimethylaminomethyleneamino)-3-(3-indolyl) ethyl acrylate, a compound of claim 1.

7. 2-(dimethylaminomethyleneamino)-3-(5-benzyloxy-3-indolyl) ethyl acrylate, a compound of claim 1.

8. 2-(dimethylaminomethyleneamino)-3-(4-cyano-3-indolyl) ethyl acrylate, a compound of claim 1.

9. 1-(dimethylaminomethyleneamino)-2-(3-indolyl)-ethylene phosphonic acid diethyl ester, a compound of claim 1.

10. A process for preparing an indole derivative of claim 1, as predominant product comprising, reacting a corresponding indole of the formula

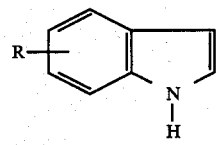

with a corresponding azabutadiene of the formula:

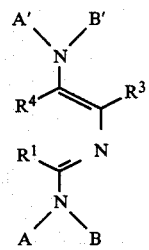

wherein A' and B', each independently is alkyl of 1 to 3 carbon atoms or together with the connecting N-atom form pyrrolidino, piperidino, morpholino or piperazino, in the presence of an acid at an effective temperature of 0° to 50° C.

11. A process of claim 10 comprising heating the indole and the azabutadiene in an organic or inorganic acid.

12. A process of claim 11 wherein the acid is formic acid, acetic acid, propionic acid, trifluoroacetic acid, phosphoric acid, polyphosphoric acid or phosphorus oxychloride.

13. A process of claim 10 wherein the acid component comprises glacial acetic acid.

14. A process of claim 13 wherein the acid component consists essentially of glacial acetic acid and trifluoroacetic acid.

15. A process for preparing a β-carboline of the formula

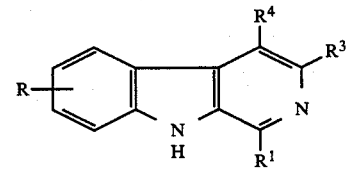

comprising
heating a corresponding compound of claim 1 to a temperature of 150°–250° C., or
heating a corresponding compound of claim 1 to a temperature of 100°–160° C. in an effective acid.

16. A process of claim 15 wherein said compound is heated in an acid which is formic acid, acetic acid, propionic acid, trifluoroacetic acid, phosphonic acid, polyphosphonic acid or phosphorous oxychloride.

17. A process for preparing a tryptophan derivative of the formula

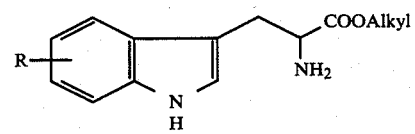

comprising hydrating a corresponding compound of claim 1 and hydrolyzing the resultant compound.

18. A process for preparing an indole derivative of claim 1, comprising, reacting a corresponding indole of the formula

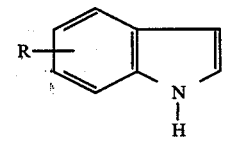

with a corresponding azabutadiene of the formula:

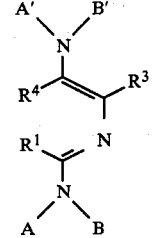

wherein A' and B', each independently is alky of 1 of 3 carbon atoms or together with the connecting N-atom form pyrrolidino, piperidino, morpholino or piperazino in the presence of an acid at a temperature effective to yield predominantly the indole derivative of claim 1.

* * * * *